United States Patent
Singh et al.

(10) Patent No.: US 6,650,422 B2
(45) Date of Patent: Nov. 18, 2003

(54) SCATTEROMETRY TECHNIQUES TO ASCERTAIN ASYMMETRY PROFILE OF FEATURES AND GENERATE A FEEDBACK OR FEEDFORWARD PROCESS CONTROL DATA ASSOCIATED THEREWITH

(75) Inventors: Bhanwar Singh, Morgan Hill, CA (US); Michael K. Templeton, Atherton, CA (US); Bharath Rangarajan, Santa Clara, CA (US); Ramkumar Subramanian, Sunnyvale, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/817,820

(22) Filed: Mar. 26, 2001

(65) Prior Publication Data

US 2002/0135781 A1 Sep. 26, 2002

(51) Int. Cl.[7] .............................................. G01B 11/00
(52) U.S. Cl. ....................................... 356/601; 356/620
(58) Field of Search .............................. 356/600, 601, 356/614, 615, 622, 625, 627, 628, 631, 637, 237.1–237.5, 364–369

(56) References Cited

U.S. PATENT DOCUMENTS

| | | | | |
|---|---|---|---|---|
| 3,782,827 A | * | 1/1974 | Nisenson et al. | 356/237.1 |
| 4,308,461 A | * | 12/1981 | Tuomaala | 250/561 |
| 4,693,607 A | * | 9/1987 | Conway | 356/627 |
| 4,844,616 A | * | 7/1989 | Kulkarni et al. | 356/237.1 |
| 4,864,150 A | * | 9/1989 | Mann et al. | 356/637 |
| 4,924,105 A | * | 5/1990 | Nagao | 250/560 |
| 5,064,291 A | * | 11/1991 | Reiser | 356/372 |
| 5,074,667 A | * | 12/1991 | Miyatake | 356/401 |
| 5,097,516 A | * | 3/1992 | Amir | |
| 5,218,193 A | * | 6/1993 | Miyatake | 250/201.4 |
| 5,272,517 A | * | 12/1993 | Tokura | 356/375 |
| 5,298,977 A | * | 3/1994 | Shintani et al. | 356/376 |
| 5,446,542 A | * | 8/1995 | Muraoka | 356/400 |
| 5,544,256 A | | 8/1996 | Brecher et al. | |
| 5,699,447 A | | 12/1997 | Alumot et al. | |
| 5,739,909 A | * | 4/1998 | Blayo et al. | 356/369 |
| 5,815,274 A | * | 9/1998 | Dlugos | 356/614 |
| 5,840,595 A | | 11/1998 | Kobayashi | |
| 6,031,614 A | * | 2/2000 | Michaelis et al. | 356/369 |
| 6,052,188 A | | 4/2000 | Fluckiger et al. | |
| 6,081,325 A | | 6/2000 | Leslie et al. | |
| 6,104,486 A | | 8/2000 | Arimoto | |

FOREIGN PATENT DOCUMENTS

| | | | |
|---|---|---|---|
| JP | 06 082 225 | * | 3/1994 |
| WO | WO 99/67626 | | 12/1999 |

OTHER PUBLICATIONS

"Dual Sensor Technology for High–Speed Detection of 0.1 Micron Defects", David Alumot, Gadi Neumann, Rivi Sherman and Ehud Tirosh, XP–002119842, SPIE, vol. 1926, pp. 570–581.

(List continued on next page.)

Primary Examiner—Frank G. Font
Assistant Examiner—Sang H. Nguyen
(74) Attorney, Agent, or Firm—Eschweiler & Associates, LLC

(57) ABSTRACT

The present invention is directed to a method and a system for non-destructively, efficiently and accurately detecting asymmetry in the profile of a feature formed on a wafer during the process of semiconductor fabrication. The method encompasses directing a beam of light or radiation at a feature and detecting a reflected beam associated therewith. Data associated with the reflected beam is correlated with data associated with known feature profiles to ascertain profile characteristics associated with the feature of interest. Using the profile characteristics, an asymmetry of the feature is determined which is then used to generate feedback or feedforward process control data to compensate for or correct such asymmetry in subsequent processing.

49 Claims, 11 Drawing Sheets

OTHER PUBLICATIONS

PCT International Search Report, International Application No. PCT/US01/43805, International Filing Date Nov. 13, 2001, 4 pgs.

"Scatterometry for the Measurement of Metal Features", In Metrology, Inspection, and Process Control for Microlithography XIV, Christopher J. Raymond, Steve W. Farrer and Scott Sucher.

Proceedings of SPIE, vol. 3998 (2000), pp. 135–145.

"Manufacturing Considerations for Implementation of Scatterometry for Process Monitoring", In Metrology, Inspection, and Process Control for Microlighography XIV, John Allgair, Dave Benoit, Rob Hershey and Lloyd C. Litt (Motorola); Ibrahim Abdulhalim, Bill Braymer, Michael Faeyrman, John C Robinson, Umar Whitney, Yiping Xu, Piotr Zalicki and Joel Seligson (KLA–Tencor Corp.), Proceedings of SPIE, vol. 3998 (2000), p. 134.

"Phase Profilometry for the 193 nm Lithography Gate Stack", In Metrology, Inspection, and Process Control for Microlighography XIV, Nickhil Jakatdar, Xinhui Niu, Junwei Bao, Costas Spanos, Sanjay Yedur and Alain Deleporte, Proceedings of SPIE, vol. 3998 (2000), pp. 116–124.

"Lithographic Process Monitoring using Diffraction Measurements", Metrology, Inspection, and Process Control for Microlithography XIV, Emmanuel M. Drege and Dale M. Byrne, Proceedings of SPIE, vol. 3998 (2000), 12 pp.

"An Integrated System of Optical Metrology for Deep Sub–Micron Lithography", Xinhui Niu, A dissertation submitted in partial satisfaction of the requirements for the degree of Doctor of Philosphy in Engineering–Electrical Engineering and Computer Sciences in the Graduate Division of the University of California, Berkeley, Spring, 1999, 153 pp.

* cited by examiner

ORIGINAL POSITION

POSITION AT ABOUT 180 DEGREES FROM ORIGINAL POSITION

SCATTEROMETRY TECHNIQUES TO ASCERTAIN ASYMMETRY PROFILE OF FEATURES AND GENERATE A FEEDBACK OR FEEDFORWARD PROCESS CONTROL DATA ASSOCIATED THEREWITH

TECHNICAL FIELD OF INVENTION

The present invention generally relates to the fabrication of a semiconductor device and more particularly to a method and a system for characterizing a symmetry of feature profiles and using that information to optimize symmetric profile patterning.

BACKGROUND OF THE INVENTION

In the semiconductor industry, there is a continuing trend toward higher device densities. To achieve these high densities there has been and continues to be efforts toward scaling down device dimensions (e.g., at submicron levels) on semiconductor wafers. In order to accomplish such high device packing density, smaller and smaller features sizes are required. This may include the width and spacing of interconnecting lines, spacing and diameter of contact holes, and the surface geometry such as corners and edges of various features.

The requirement of small features with close spacing between adjacent features requires high resolution photolithographic processes. In general, lithography involves the transfer of a pattern or image from one medium to another, as from a mask to a wafer. In particular, a mask can be used to protect one area of the wafer while working on another. For example, a photoresist is applied to a wafer and aligned to a mask. Then light such as ultraviolet radiation can be projected through the mask, thereby exposing the photoresist with the mask pattern. The wafer is then developed to remove the exposed photoresist and baked to harden the remaining photoresist pattern. Areas not covered by the hardened photoresist are then etched away, and the wafer is inspected to ensure the image transfer from the mask to the top layer is correct. This process is repeated several times until all active devices and features have been formed.

During the fabrication process of a semiconductor, for example, during etching, thin film deposition or chemical mechanical polishing, features may become non-uniform in their profile structures. For example, the etching away of a polysilicon feature such as a gate may result in the feature having an asymmetric profile such that one side of the feature is situated at about a 90° angle to the substrate but the opposite side of the feature is situated at an angle greater than or less than the first side. This asymmetry in the feature profile may lead to performance problems or degradation, especially in extremely small devices, caused by the shallow or malformed features in the front end. Inevitably, the device may exhibit poor resistance or conductivity or fail other types of parametric and/or functional criteria, and may thus be rendered sub-standard due to the asymmetric feature profiles.

Therefore, in a production line of semiconductor devices, there is a need to examine the profile of structures such as a feature formed on a wafer quickly, without contacting or destroying the structure prior to the completion of the semiconductor device. There is also a need to optimize fabrication process parameters during semiconductor production to provide more exact control and detection of asymmetric feature profiles.

SUMMARY OF THE INVENTION

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

The structural profile of features formed on a wafer may affect the conductivity and overall performance of a semiconductor device. Asymmetrically formed features may result in reduced performance of the semiconductor device. Thus there is a need to obtain information on feature profiles to determine the quality and preciseness of a fabrication process to prevent asymmetric feature profiles.

The present invention is directed to a method and a system for non-destructively, efficiently and accurately detecting asymmetry in the profile of a feature formed on a wafer during the process of semiconductor fabrication. The system comprises a light source, a stage for a patterned wafer sample, a detector, a processor system including a memory and a processor associated therewith, and a display unit. According to another aspect of the present invention, the system is placed in-situ a semiconductor fabrication line for immediate detection and control to optimize subsequent feature formation.

The method encompasses directing a beam of light or radiation at a first side of a feature. A detector captures and measures a reflected beam associated with the first side of the feature. The light source or the feature is rotated (e.g., about 180 degrees) with respect to the other from an original position and a beam of light is now directed to a second side of the feature. A detector again captures and measures a reflected beam associated with the second side of the feature and the two sets of measurements (from the first and the second sides) are correlated by a processor system using a predetermined correlation threshold. Once correlated, the symmetry or asymmetry of a feature profile is determined.

In particular, the present invention describes a method of detecting asymmetry of a feature profile and comprises placing a patterned wafer with at least one feature formed (e.g., a grating) thereon into a characterization chamber. An incident beam of radiation is then directed at a first side of a feature and a first reflected beam associated with the first side of the feature is detected. An incident beam of radiation is then directed at a second side of the feature and a second reflected beam associated with the second side of the feature is detected. Using the data collected from the first side and the second side of the feature, a pattern profile is determined. By analyzing the determined pattern profile, a type and degree of feature asymmetry is ascertained and utilized to generate feedback or feedforward control data to account and adjust for such asymmetry.

Another aspect of the method comprises directing an incident beam of polarized light at a first side of a feature and detecting a reflected beam to determine a change in the state of polarization before and after reflection. The change in polarization is then employed to ascertain properties associated with the reflecting boundary (e.g., the feature profile). A light source or a stage is then rotated, for example, about 180 degrees from its original position, causing the beam of light to be directed at a second side of the feature and the measurement is performed again.

Another aspect of the present invention allows for direction of a broadband wavelength range of incident light on the feature of interest in a direction generally normal to the wafer surface. The reflected light intensity as a function of wavelength is then detected. The reflection data is then compared to a database of reflection profiles containing numerous reflection signatures associated with different known feature profiles. As a result of the comparison, the profile of the feature of interest and its associated asymmetry is identified. Such identification is then used to generate feedback or feedforward process control data to compensate or correct for such asymmetry in subsequent processing.

In accordance with yet another aspect of the present invention, scatterometry is employed to ascertain the asymmetry of a test structure such as a grating. An incoming light spectra reflects off of the test structure and a detector collects a reflected light intensity and phase profile as a function of wavelength. The profile data is then compared with a database of intensity and phase signatures associated with known feature profiles to identify the profile of the test structure. This process is then repeated for an opposite side of the test structure to ascertain an asymmetry associated therewith. The asymmetry determination is then employed to generate feedback or feedforward control data to compensate for the asymmetry or modify the process to prevent subsequent feature asymmetry.

The invention extends to features hereinafter fully described and features particularly pointed out in the claims. The following detailed description and the annexed drawings set forth in detail certain illustrative examples of the invention. These examples are indicative of but a few of the various ways in which the principles of the invention may be employed. Other ways in which the principles of the invention may be employed and other objects, advantages and novel features of the invention will be apparent from the detailed description of the invention when consider in conjunction with the drawings.

DETAILED DESCRIPTION OF THE INVENTION

Figure 1:
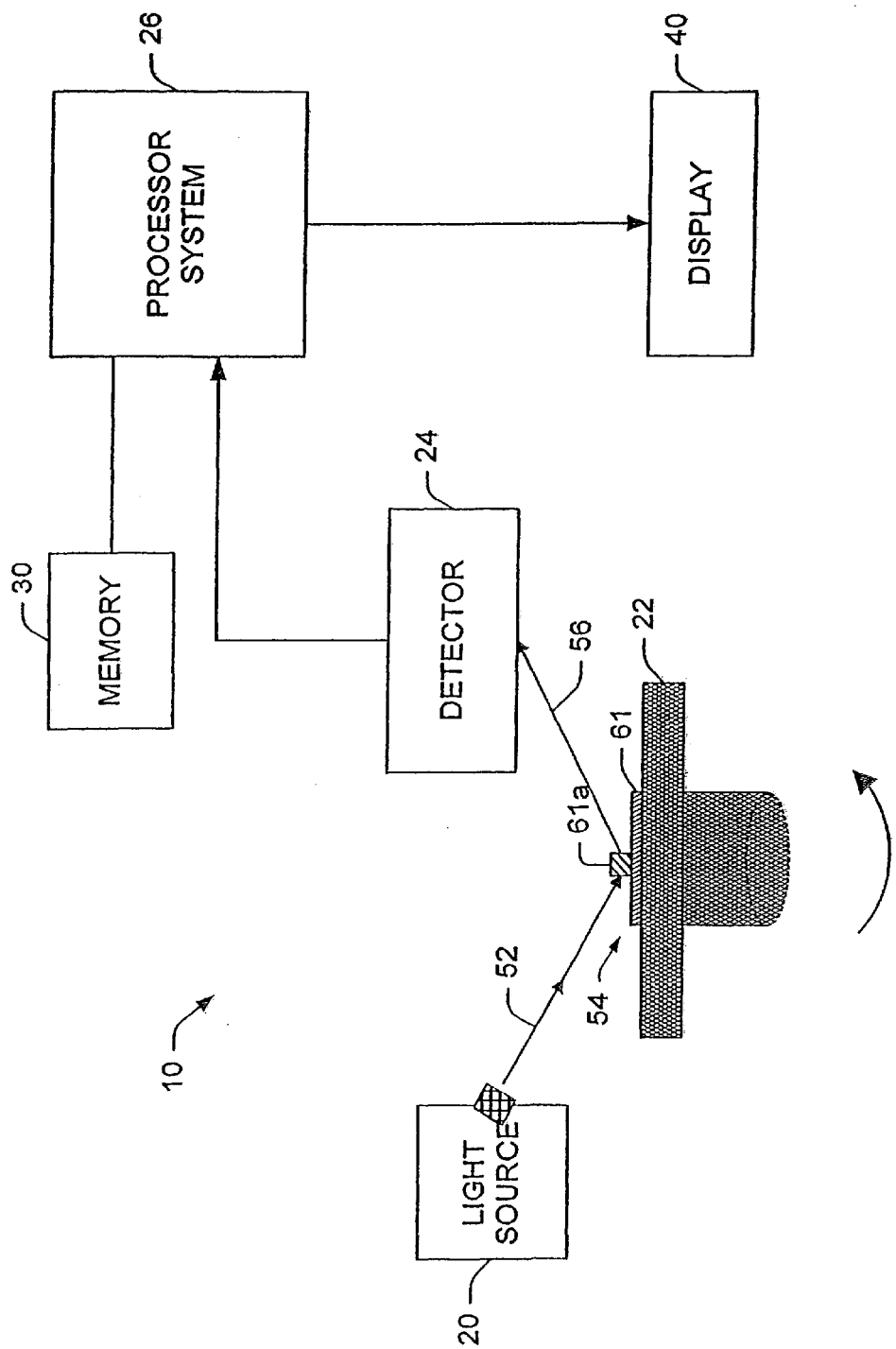
FIG. 1 is a partial block diagram illustrating an exemplary detection system according to the present invention.

The present invention will now be described with reference to the drawings wherein like reference numerals are used to refer to like elements throughout. In accordance with one aspect of the present invention, a method will be described with reference to the detection of an asymmetric profile of a feature formed on a wafer employing ellipsometry, reflectometry or scatterometry. Upon ascertaining the degree of asymmetry associated therewith, the method further comprises generating feedback or feedforward process control data to compensate or adjust subsequent processing to mitigate such asymmetry. It should be understood that the description of these aspects are merely illustrative and that they should not be taken in a limiting sense.

Referring now to the figures, several aspects of the present invention are presented. FIG. 1 is a schematic illustration of an exemplary system using an optical technique such as ellipsometry, reflectometry or scatterometry to determine a pattern profile or to characterize a symmetry of a feature profile. It is to be appreciated that the system shown in FIG. 1 is not necessarily drawn to scale to illustrate the teachings of this invention.

Ellipsometry is one tool which can be employed to characterize the symmetry or lack thereof of a feature profile. Ellipsometry is an optical technique devoted to the analysis of surfaces. It is based on the measurement of the variation of the polarization state of the light after reflection on a plane surface. The strong advantages of ellipsometry are its non-destructive character, its high selectivity due to the measurement of the phase of the reflected light, its large measurement range and the possibilities to control real time complex processes.

Spectroscopic ellipsometry employs linearly polarized incident light and exploits the fact that the component waves of incident light experience different amplitude attenuations and varying phase shifts upon reflection from a surface. Therefore the state of polarization changes upon reflection upon the surface. In accordance with one exemplary aspect of the present invention, an ellipsometer measures a phase of a reflected light beam as a function of wavelength and an intensity of a reflected light beam as a function of wavelength, the analysis of which corresponds to a particular structure. A detector collects the phase and intensity data and then communicates that information to a processor system where the data is calculated and saved into memory for future use. The information is then displayed by a monitor, a printer or any other displaying device. The information can also be fed back into fabrication process parameters to optimize subsequent feature formation.

In particular, using ellipsometry, an incident light, for example, light having multiple wavelength components such as about 100 nm to about 1000 nm, with an incident angle and a polarization angle, reflects off of a feature or test structure (e.g., a grating). The reflected light exhibits a change in its electric field components, its phase and its polarization due to the different between the refractive index and reflectance between the test structure and the wafer substrate. As a result, a complex coefficient ration may be obtained.

The profile of the test feature which is collected via the detector and is later compared against a database of data corresponding to known feature profiles to ascertain the profile of the test structure of interest. By repeating such analysis from the other side, feature profile data associated with both sides of the feature is determined and an asymmetry associated therewith is identified. Using such asymmetry information, a processor is used to determine process anomalies that may be associated with contributing to such asymmetry. Feedback or feedforward process control data is then generated to compensate or correct subsequent processing to mitigate for the detected asymmetry.

According to another exemplary aspect of the present invention, spectroscopic reflectometry employs a normal-directed incident beam of light containing multiple frequency components, for example, about 100 nm to about 1000 nm, to collect a reflected light intensity distribution over the wavelength range. That is, a light is directed to a test structure (e.g., a grating) in a generally normal or perpendicular fashion, and an intensity profile, which is a function of wavelength, is collected from the reflected light. Since the incident light is generally perpendicular to the surface, data regarding the profiles of both sides of the feature may be ascertained (e.g., assuming both sides of the feature(s) of interest exhibit non-perpendicular profiles which are not re-entrant). Accordingly, data associated with the asymmetry of the feature profile may be collected in a single measurement. The intensity distribution data is then compared to a database of intensity distributions associated with known feature profiles to identify the profile of the structure of interest. Such information is then utilized to ascertain the asymmetry of the feature of interest and, using such asymmetry information, a processor is used to determine process anomalies that may be associated with contributing to such asymmetry. Feedback or feedforward process control data is then generated to compensate or correct subsequent processing to mitigate for the detected asymmetry.

Scatterometry is another tool which can be employed to characterize a feature profile. Scatterometry is a technique that involves directing a light beam, typically a laser, on an area to be characterized and measuring the angular distribution of the light that is elastically scattered from that area. An exemplary system may employ one or more light sources arranged to project light on respective portions of a feature and one or more light detecting devices to collect light reflected by the feature. A processor system is operatively coupled to one or more detecting devices. The detector device measures and the processor system calculates a power spectral density (PSD) as a function of spatial frequency. PSD is a measure of scattered power per unit of spatial frequency.

FIGS. 1–6 of the present invention illustrate a method and a system using ellipsometry, reflectometry or scatterometry for gaining information on the structural profile of features formed on a wafer or substrate to optimize processing and performance of semiconductor devices and to reduce the variability in feature profile asymmetry.

In FIG. 1, a characterization system 10 comprises a light source 20, a stage 22, a detector 24, a processor system 26 having a memory 30 associated therewith, and a display unit 40, wherein the processor 26 is associated therewith and/or coupled to the detector 24. The light source 20 is positioned to direct an incident beam of radiation 52 at a sample 54. The sample 54 comprises a wafer 61 having a feature 61a formed therein or thereon. It should be appreciated that the wafer 61 may contain more than one feature, as may be desired.

The stage 22 comprises a rotating base or other mechanism which will cause the stage to rotate. In another aspect of the present invention, the stage 22 comprises a mechanism for rotating the sample 54 while maintaining the position of the stage 22. Alternatively, the stage 22 may be fixed and the light source 20 may be rotated about the sample 54. The detector 24 detects a reflected beam 56 and communicates this data to the processor system 26. The processor system 26 collects this data and determines a pattern profile of a feature using the collected data. The determined pattern profile can then be sent to the display unit 40, stored in the memory 30 of the processor system, or fed immediately back into the production line to alter the fabrication process of subsequent features.

As illustrated in FIG. 1, the light source provides incident light at an angle with respect to the wafer 61. Although FIG. 1 illustrates an angle of incidence between 0° and 90°, it should be understood that the angle may be normal or generally perpendicular to the wafer 61, for example, in instances where a reflectometry analysis is conducted.

Figure 2:
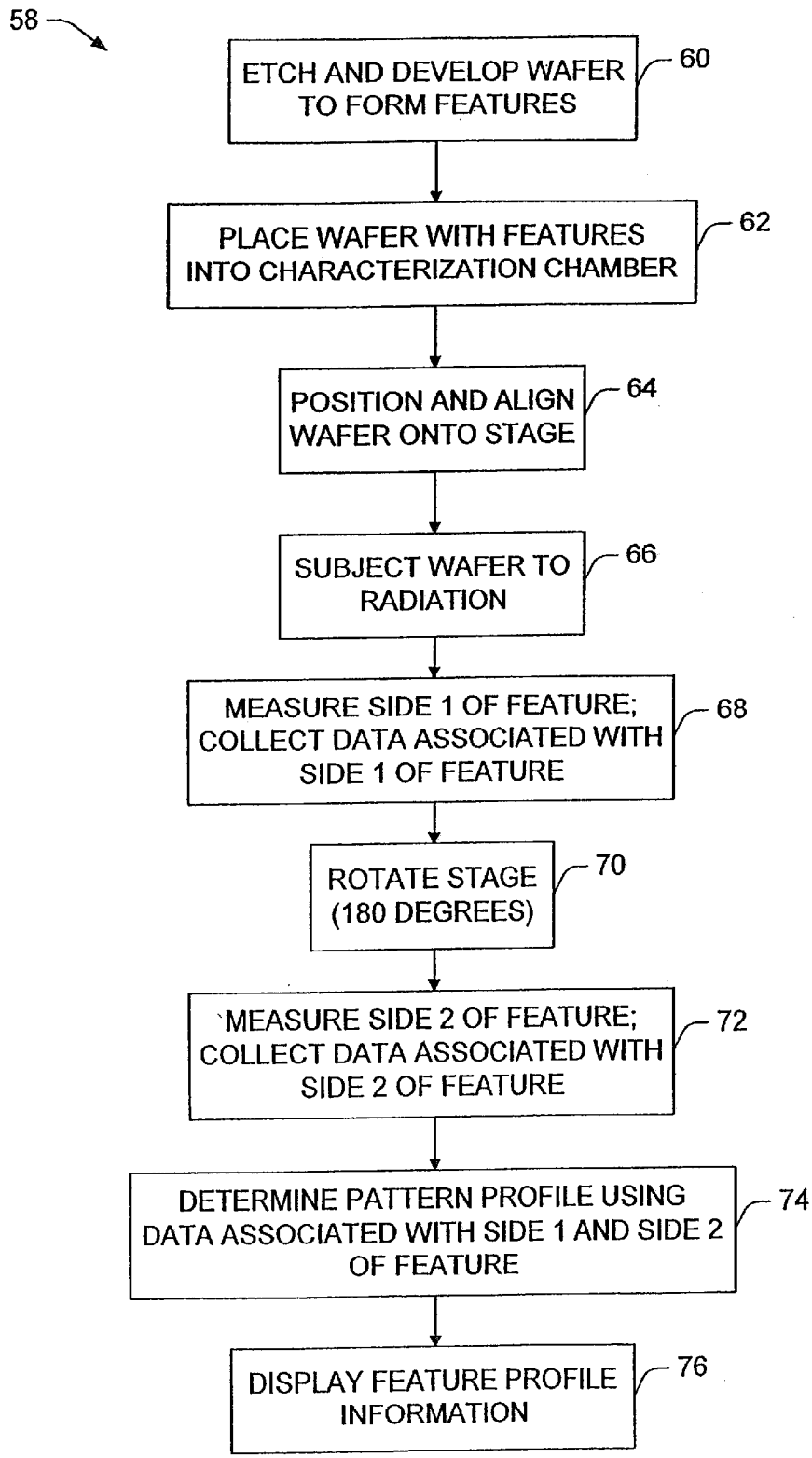
FIG. 2 is a flow chart illustrating a method for characterizing a feature profile formed on a wafer, measuring a first and second side of the feature, and then determining its pattern profile.
Figure 2A:
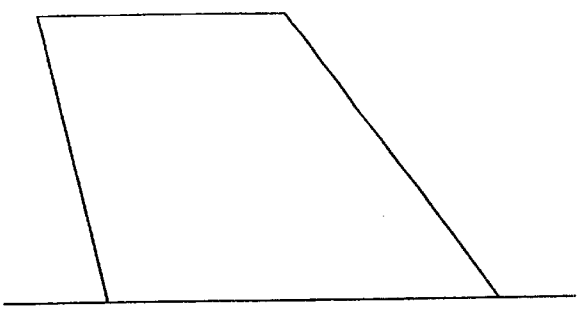
FIGS. 2a through 2e are schematic illustrations of exemplary pattern profiles associated with a feature formed on a wafer.
Figure 2B:
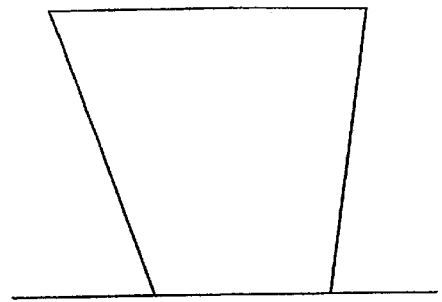
Figure 2C:
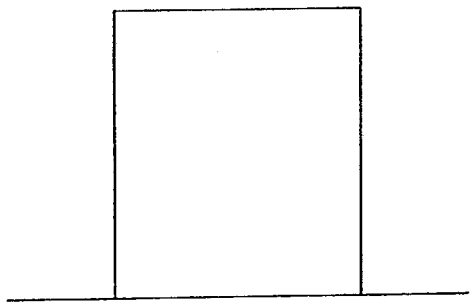
Figure 2D:
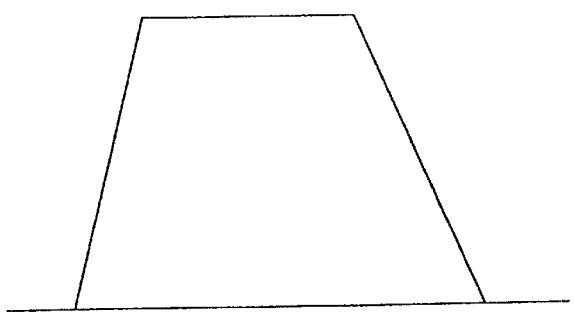
Figure 2E:
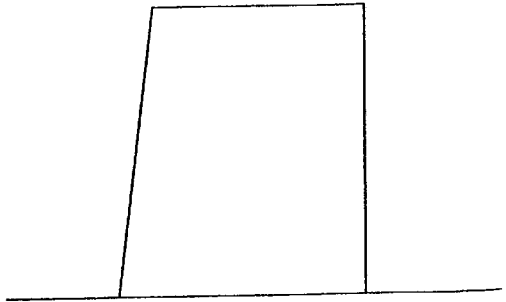

FIG. 2 is a flow chart illustrating a method 58 for determining a pattern profile of a feature formed on a wafer using, for example, the system shown in FIG. 1. The method 58 begins at step 60 in which a wafer 61 is processed, for example, etching a film (e.g., polysilicon), or developing an exposed photoresist, to form a patterned feature 61a thereon (FIG. 1). For example, a gate structure may be formed on a wafer or a grating. Other features which can be formed on a wafer include a trench or a via, for example. In step 62, the patterned wafer 61 is placed into a characterization chamber. At step 64, the etched wafer 61 is positioned and aligned onto the stage 22 (FIG. 1). The etched wafer 61 is subjected to radiation 52 in step 66 (FIG.1). For example, for an ellipsometry analysis, the radiation may be an incident beam of polarized light at a range of wavelengths, such as a range of about 100 nm to about 1000 nm. The incident beam of radiation 52 is directed generally at a side of the feature 61a. Alternatively, for a reflectometry analysis the incident beam (e.g., unpolarized light) is incident upon the feature 61a in a generally perpendicular fashion.

At step 68, a reflected beam associated with a first side of the feature 61a is detected and measured using, for example, the detector 24. In step 70, the stage 22 is rotated from an original position (see, e.g., FIGS. 3a and 3b). For example, the stage can be rotated about 180 degrees from an original position such that a second side exposed to radiation is a side opposite the first. Alternatively, the source of radiation 52 can be rotated about the feature 61a so as to be directed generally at a second side of the feature. In step 72, a reflected beam associated with the second side of the feature 61a is detected and measured.

In one aspect of the invention, the incident beam of radiation 52 is directed to substantially the entire side of the feature. In another aspect of the invention, the incident beam of radiation 52 is directed to portions of a side associated with the feature, wherein the irradiated portions of the first side substantially correspond to the irradiated portions of the second side. The desired portions of a side associated with a feature to be irradiated may differ depending on the type of feature.

In accordance with one exemplary aspect of the invention, with a reflectometry analysis, the incident radiation is directed toward the wafer in a generally perpendicular fashion and consequently the steps of directing radiation to different sides is not necessary, nor is a rotation of the feature necessary since light will reflect off both sides of the feature 61a when normally incident thereon (for non-perpendicular, non-re-entrant profiles), and thus data associated with both sides of the feature 61a may be collected in a single step.

The data associated with the first and second sides of the feature 61a are collected, for example, by the processor system 26 (FIG. 1). At step 74, the method 58 determines a pattern profile using the collected data associated with the first and second sides of the feature 61a. For example, the pattern profile of a gate structure formed on the wafer could be determined as shown in FIGS. 2a, 2b, 2c, 2d, or 2e. The method ends at step 76 in which a determined profile structure of the feature 61a is displayed to an operator, for example. This information can also be kept or maintained in a database for further analysis or displayed using any other type of output device such as a monitor or a printer.

Figure 3:
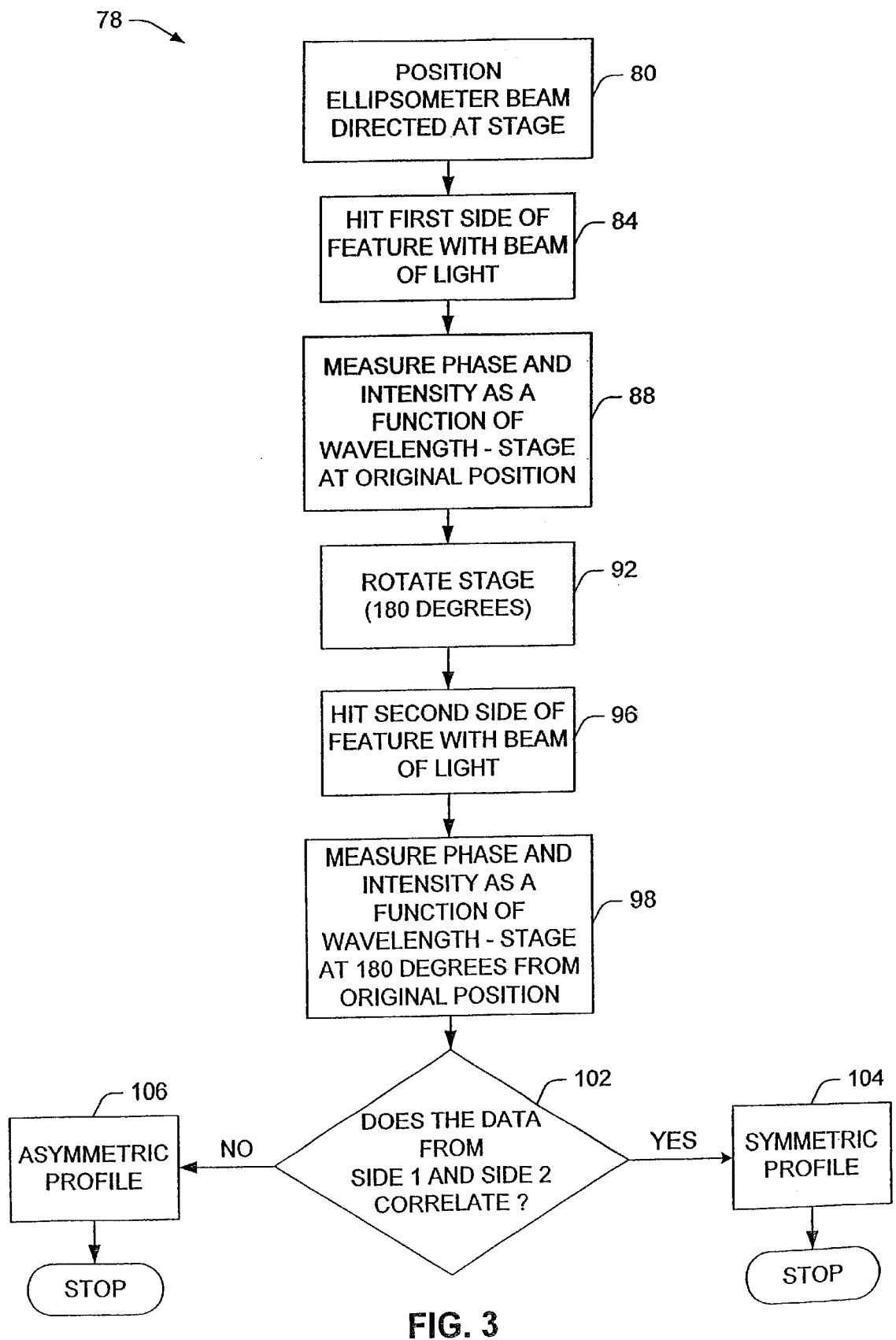
FIG. 3 is a flow chart illustrating a method for characterizing a profile of a feature formed on a wafer using ellipsometry.
Figure 3A:
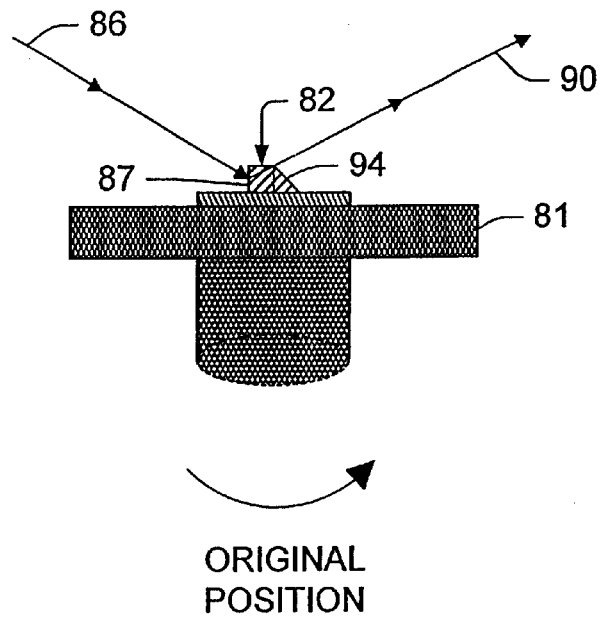
FIGS. 3a and 3b are schematic illustrations demonstrating aspects of a method of the invention as described in FIG. 3.
Figure 3B:
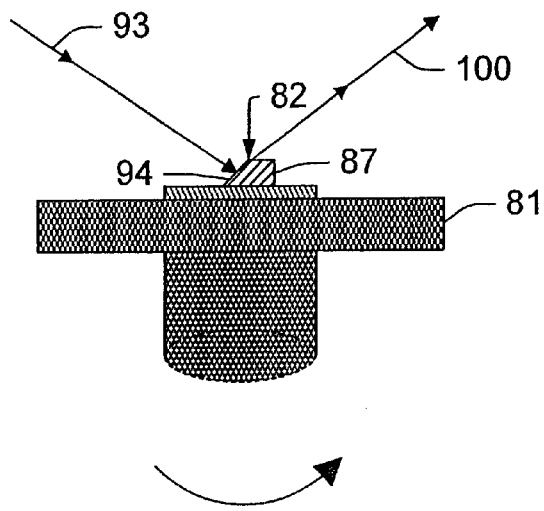

In accordance with one exemplary aspect of the present invention, the characterization process described in FIG. 2 is performed using an ellipsometer in a method 78. Referring to FIG. 3 together with FIGS. 3a and 3b, the method 78 begins at step 80 in which an incident beam of polarized light having a predetermined range of wavelengths is directed at a stage 81 whereupon a wafer with a feature 82 has been aligned. The exemplary range of wavelengths of the incident light is about 100 nm to about 1000 nm. At step 84, a beam of polarized light 86 is directed generally at a first side 87 of the feature 82 (FIG. 3a). It should be appreciated that the term "generally" indicates that the beam of light 86 may be directed to any area associated with the first side 87 of the feature or a second side 94, as the case may be. It should also be appreciated that a filter (not shown) may be used to eliminate any background "noise" associated with this method.

Figure 4A:
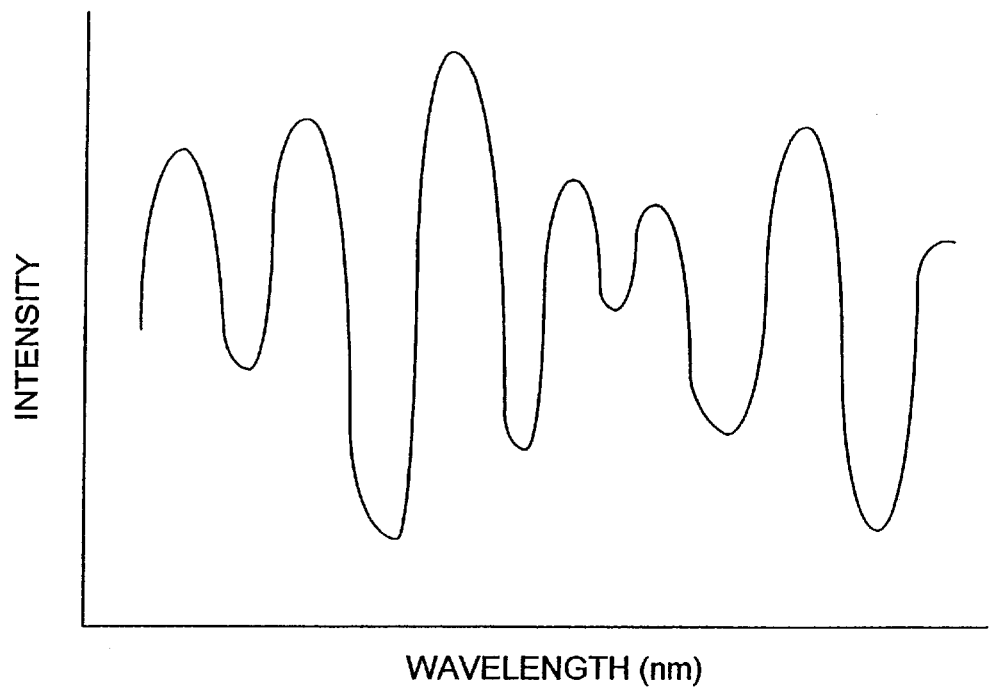
FIGS. 4a and 4b are exemplary graphs of intensity and phase, respectively, as a function of wavelength associated with a side of a feature measured by an ellipsometer.
Figure 4B:
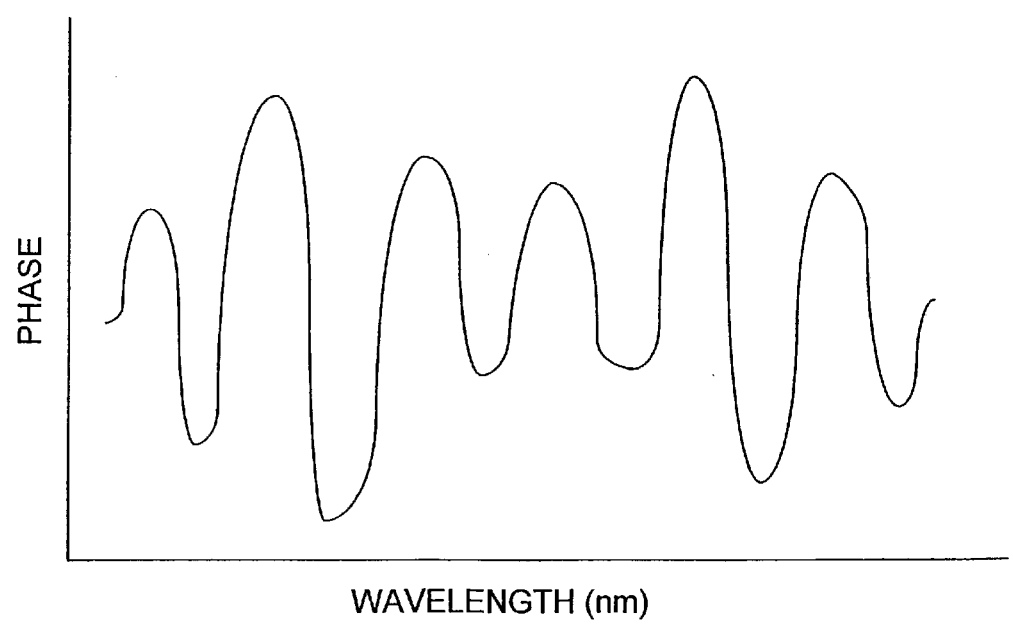

In step 88, a detector detects and measures an intensity and a phase of a first reflected beam 90 as a function of wavelength. An example of this type of data is illustrated in FIGS. 4a and 4b, respectively. As a further note, detection may be accomplished using any detector known in the art and suitable for achieving the objectives of this invention. In step 92, the stage 81 is rotated about 180 degrees from its original position. An incident beam of polarized light 93 having a predetermined range of wavelengths is directed toward a second side 94 of the feature 82 (step 96). Again, the exemplary range of wavelengths is about 100 nm to about 1000 nm.

At step 98, a detector detects and measures an intensity and a phase of a second reflected beam 100 as a function of wavelength. This data is communicated to and collected by a processor system 26 (FIG. 1). In step 102, a processor system 26 (FIG. 1) determines whether the data collected from the first side 87 and the second side 94 of the feature 82 correlate. For example, the intensity data and the phase data can each be correlated for the first and second sides, respectively. In one aspect of this invention, "correlate" is defined as a statistical correlation analysis between the data of the first and second sides. Symmetry or asymmetry is determined according to a correlation threshold (e.g., symmetry if correlation is greater than 0.9 or some other predetermined threshold).

According to another aspect of this invention, "correlate" is defined as comparing the determined pattern profiles of the first side and the second side, respectively, for example, by a comparison of the pattern profiles from the first and second sides to determine whether the profile of the feature is asymmetric via the processor (e.g., within X° of one another or Y% of one another, wherein X or Y is predetermined according to characterization criteria). If the question is answered in the affirmative (YES), then the feature is judged acceptable (step 104); and the method 78 ends. However, if the amount of correlation is insufficient, then the method proceeds to step 106. Once a feature profile is determined to be asymmetric, various steps can follow. For example, the information may be provided to an operator for further testing of the subject wafer, the wafer may be discarded from the production line either manually or automatically, or the data collected from the wafer may be used to optimize one or more process parameters of the semiconductor fabrication process, as will be described in greater detail infra.

Figure 5:
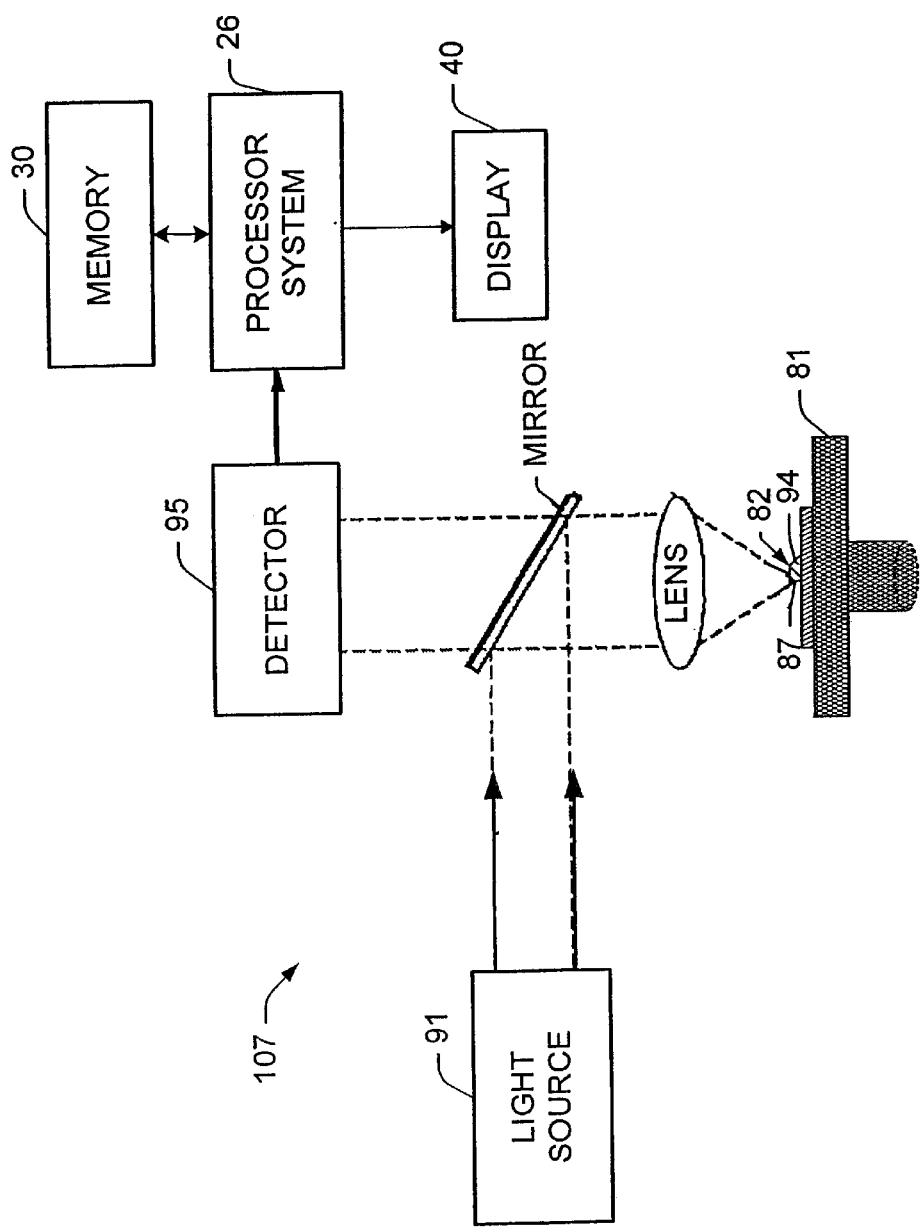
FIG. 5 is a partial block diagram illustrating an exemplary detection system according to the present invention.
Figure 5A:
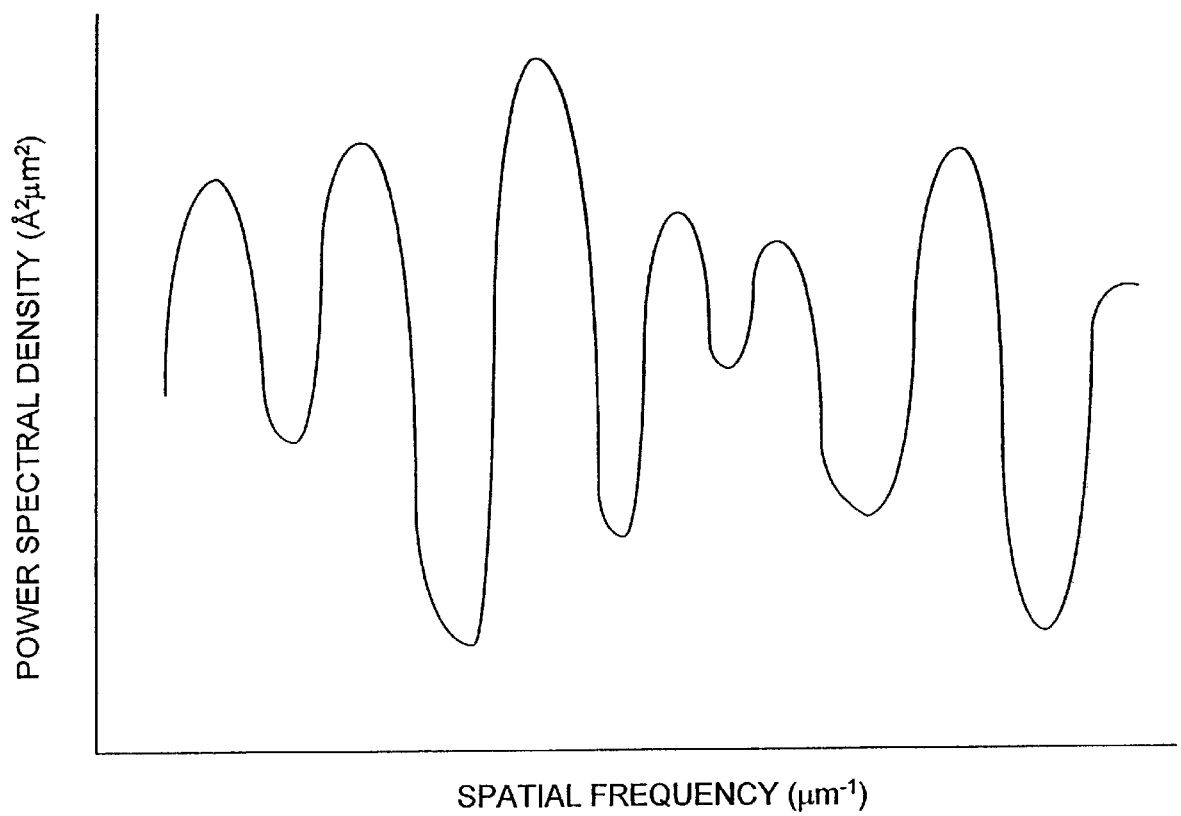
FIG. 5a is a graph of power spectral density (PSD) as a function of spatial frequency for a scatterometer.

With reference to the method 78 as described in FIG. 3, a method 109 represents another aspect of the present invention which encompasses using a scatterometer to characterize a feature profile as symmetric or asymmetric. An example of a scatterometer system 107 suitable for the characterization process is shown in FIG. 5. The method 78 and the method 109 differ in a few key respects. For example, the method 109 provides for directing an incident beam of nearly collimated light 91 (FIG. 3, Step 80, 84) toward a first side of a feature 82. In the following step, a detector 95 detects a first reflected beam and a processor calculates a power spectral density (PSD) as a function of spatial frequency. PSD is a measure of scattered power per unit of spatial frequency. An example of such data associated with a side of a feature is illustrated in FIG. 5a. Method 109 continues accordingly as described above in FIG. 3 to determine whether the feature profile is symmetric or asymmetric using the scatterometric data.

Alternatively, one or more incident beams of light may be directed at a side associated with a feature either in succession or simultaneously. In another aspect of the present invention, one or more detectors may be used to collect relevant data. In yet another aspect of the present invention, the light source 91 may be stationary with respect to the stage 22. In still another aspect of the present invention, the light source 91 may be non-stationary with respect to the stage 22 such that the detector 95 detects reflected light at timed intervals as the light source 91 rotates around the feature 82.

In accordance with one exemplary aspect of the present invention, the above discussed systems and methods allow a use to identify whether a patterned feature exhibits an asymmetric feature profile. In addition to simply ascertaining whether asymmetry exists, the systems and methods may also be operable to ascertain an amount of asymmetry between the opposing sides of a feature via, for example, use of a database containing known profile data signatures (e.g., via correlation).

Figure 6:
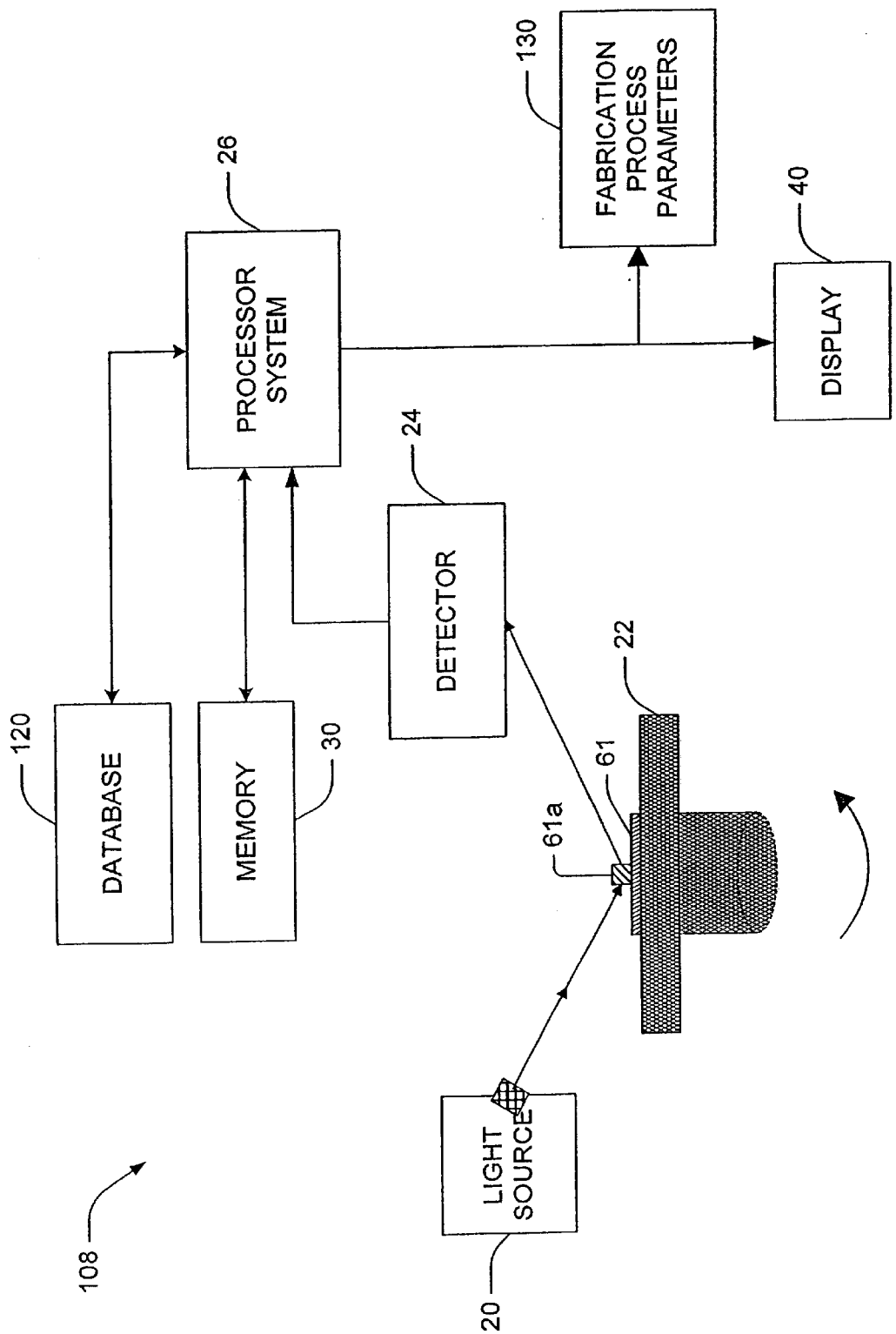
FIG. 6 is a partial block diagram illustrating a detection system employing a database according to the present invention.

Referring now to FIG. 6, an exemplary illustration of a characterization chamber system 108 for determining a pattern profile of a feature using a database is shown. FIG. 6 also illustrates placing the system 108 in-situ for immediate detection and control of asymmetric feature profiles during semiconductor fabrication 130, which will be discussed later. According to FIG. 6, a database 120 is connected to and communicates with the processor system 26. The database comprises sets of data corresponding to known feature profiles. The types of data depend on the type of device used to conduct the characterization of a feature. For example, if one uses an ellipsometer to characterize a feature profile (FIG. 3), then the database comprises sets of phase and intensity as a function of wavelength associated with known feature profiles, wherein one set of phase and intensity as a function of wavelength corresponds to a side of a feature having a known side profile of that side.

Likewise, if a reflectometry system/method is being employed, data sets comprising reflectance intensity as a function of wavelength may be measured and compared against a database of intensity distributions associated with known feature profiles. Lastly, for example, if a scatterometry system/method is utilized, intensity/phase distributions or power spectral density functions may be measured and/or calculated and compared against a database of such data signatures associated with known feature profiles.

As discussed above, the asymmetry of the profile is determined by determining the profile characteristics of each side of a feature by comparing collected data associated with the feature of interest to a database of data signatures associated with known feature profiles and then ascertaining the asymmetry using such information for both sides of a feature. According to another exemplary aspect of the present invention, the database of signatures associated with known feature profiles may be utilized to train a neural network. Subsequently, a data set associated with a feature under analysis may then be put into the trained neural network which will then provide a determination of the state of the feature profile. Using the determination associated with both sides of the feature, the processor is operable to determine an asymmetry associated with the feature of interest.

Figure 6A:
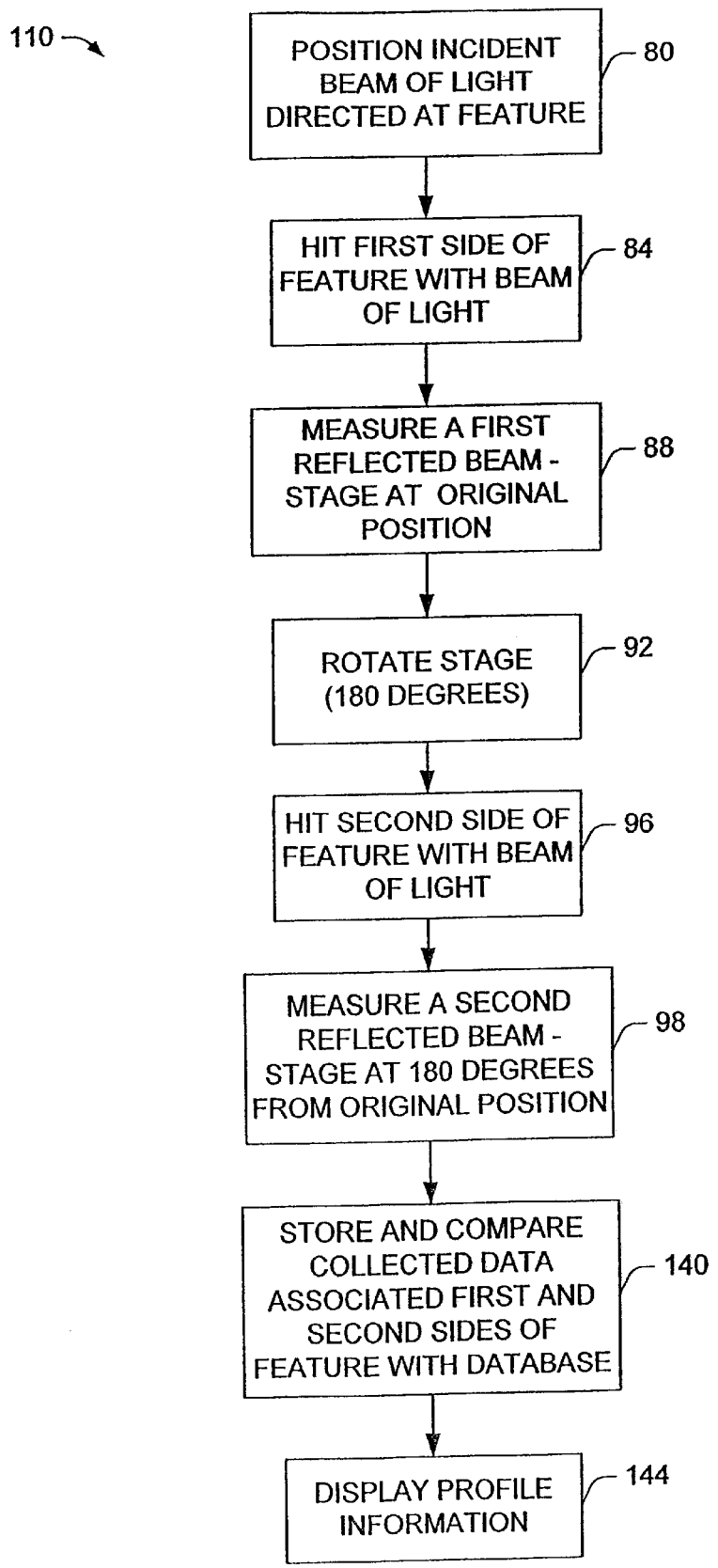
FIG. 6a is a flow chart illustrating a method for characterizing a feature profile using a database.

Turning to FIG. 6a, a flowchart which illustrates a method 110 for characterizing a symmetry of a feature profile using the database 120 (FIG. 6) is shown. The method 110 begins with steps similar to method 78; for example, steps 80 through 98 (FIG. 3). After performing a step similar to step 98 (FIG. 3), method 110 continues to step 140 in which the database 120 is compared to the phase and intensity data (e.g., for an ellipsometry or scatterometry system/method) associated with a first side and a second side of a feature, respectively. Following step 140, the profile information is displayed or communicated (step 144). It is to be appreciated that the process described in FIG. 6a is merely exemplary of performing the characterization process using a database. For example, the comparison between the collected data and the database could occur after the first side is measured and again after the second side of the feature is measured. In addition, the comparison may comprise a statistical correlation in which a match is found for any correlation that exceeds a predetermined threshold. Further, if multiple data sets match the correlation, the data set which exhibits the highest correlation may be selected.

Alternatively, if reflectometry is being employed, simply an intensity distribution data set may be utilized. If scatterometry is being employed, not only may the intensity and phase distribution data be used, but a power spectral density may be calculated and utilized, as may be desired.

Figure 6B:
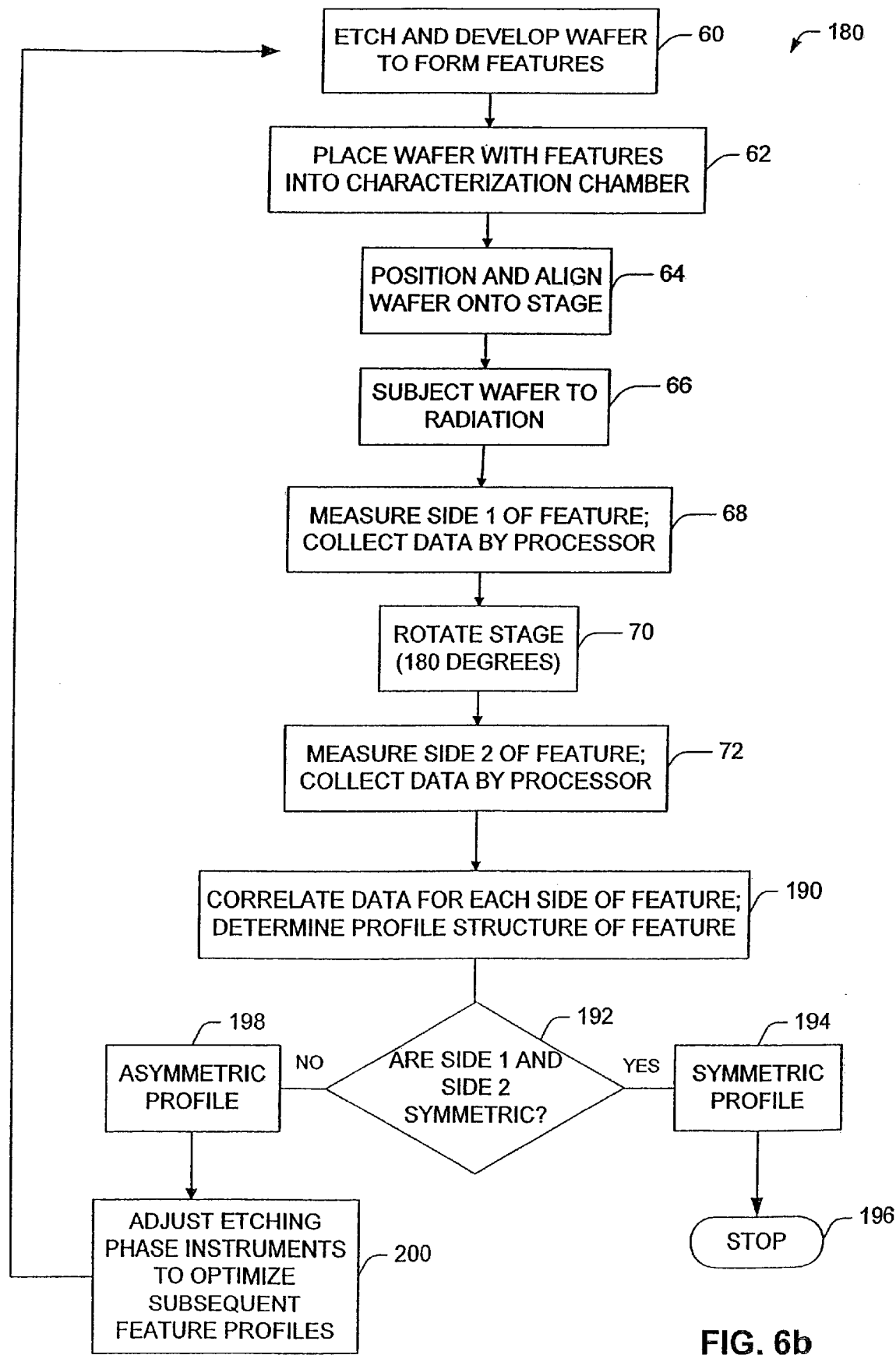
FIG. 6b is a flow chart illustrating a method for characterizing a feature profile for immediate feedback into fabrication process parameters to optimize subsequent feature formation.

According to another aspect of the present invention, FIG. 6b illustrates an exemplary method 180 in which information associated with a feature profile, which is determined to be asymmetric, is immediately fed back or fed forward into fabrication process parameters 130 to optimize semiconductor formation. For example, the method 58 as described in FIG. 2 is placed in-situ a semiconductor fabrication line.

Various types of process conditions may contribute to feature asymmetry. For example, in a chemical-mechanical polish (CMP) process, asymmetry may result from slurry composition, polish pad(s) condition or wear, polish pad movement control, etc. In such circumstances, an identification of profile asymmetry may be utilized by the processor to generate feedback control data to alter one or more of the above process parameters to reduce such asymmetry in subsequently formed features.

In accordance with another exemplary aspect of the present invention, profile asymmetry may be caused by lens aberrations such as coma. In such circumstances, the asymmetry determination by the processor may be utilized by the processor to vary an exposure condition globally or adjust a pupil filter to alter an intensity or phase of light globally or locally in one or more portions of the image field to thereby compensate for the aberration for subsequently formed features.

In accordance with yet another exemplary aspect of the present invention, asymmetric features such as polysilicon gates can affect subsequent ion implantation steps, thereby negatively causing non-uniformity in spatial doping concentration in the source/drain regions. In such circumstances, the present invention contemplates utilizing the asymmetry information determined by the processor to generate feedforward process control data to vary a subsequent ion implantation step to compensate for the profile asymmetry and thereby establish substantially spatially uniform source/drain regions.

For example, if one side of a polysilicon gate structure is determined to have a substantially more sloped sidewall than the other side of the gate, a tilt implant may be associated with the implantation of that side of the gate so as to ensure more dopant under a portion of the shaped profile than would otherwise exist in that region with a conventional implantation step. This and other type of feedforward compensation adjustments may be employed by the processor via process control data in view of the asymmetry determination. For example, an amount or type of process control data may be a function of an amount of asymmetry determined, as may be desired.

The method 180 begins with many similar steps as previously described in FIG. 2; for example, steps 60 through 72. Following performance of the similar step 72, the method 180 continues with step 190 in which collected data associated with a first side and a second side of a feature are correlated as specified in the method 58. Alternatively, a database such as is used in method 110 could be employed to determine a profile of the feature (step 190).

In step 192, a processor system must determine if the first side and the second side of the feature are symmetric. If the response is in the affirmative (YES), then the profile is determined symmetric (step 194) and the method 180 stops (step 196). However, if the response is negative, then the profile is determined asymmetric (step 198) and the collected data associated with this feature is fed back into fabrication process parameters 130 so that adjustments are made to optimize subsequent feature formation (profiles) (step 200).

For example, as described above, changing fabrication process parameters includes altering an etching process such as altering a plasma chemistry, pressure, etc. in a plasma etching process to increase or decrease a slope of a sidewall of the feature, thereby improving a symmetry of subsequent features. Alternatively, changing fabrication process parameters may include altering one or more factors associated with chemical mechanical polishing (CMP) pads, the CMP slurry, etc. to increase or decrease an amount of polishing on either the first or the second side or both sides of the feature, or altering an alignment of the wafer to compensate for a coma effect associated with a stepper lens during an etching process. It should be appreciated that other process parameters that influence feature formation may also be altered and such alterations are contemplated as falling within the scope of the present invention. In addition, more than one process parameter could be altered depending on the information associated with the asymmetric feature profile.

It is also to be appreciated that the methods 78 and 109 (FIG. 3) could also be placed in-situ a semiconductor fabrication line to perform the method 180.

In another aspect of the present invention, a trained neural network is incorporated into a processor system to characterize the symmetry associated with a feature profile. For example, a trained neural network could be introduced into the methods described above in FIG. 3, 6a or 6b to determine the symmetry of a feature profile.

Although the invention has been shown and described with respect to certain aspects, equivalent alterations and modifications will occur to others skilled in the art upon the reading and understanding of this specification and the annexed drawings. In particular regard to the various functions performed by the above described components (systems, devices, assemblies, etc.), the terms used to describe such components are intended to correspond, unless otherwise indicated, to any component which performs the specified function of the described component (i.e., that is functionally equivalent), even though not structurally equivalent to the disclosed structure that performs the function in the herein illustrated exemplary aspects of the invention. In addition, while a particular feature of the invention may have been disclosed with respect to only one of several aspects, such feature may be combined with one or more other features of the other aspects as may be desired and advantageous for any given or particular application. Furthermore, to the extent that the term "includes" is used in either the detailed description and the claims, such term is intended to be inclusive in a manner similar to the term "comprising."

What is claimed is:

1. A method of detecting asymmetry of a feature profile comprising:
    directing a first incident beam of radiation having multiple wavelength components generally at a first side of a feature on a substrate, wherein the first incident beam is at a non-perpendicular angle to the substrate;
    detecting a first reflected beam associated with the first side of the feature;
    directing a second incident beam of radiation having multiple wavelength components generally at a second side of the feature on the substrate, wherein the second incident beam is at a non-perpendicular angle to the substrate;
    detecting a second reflected beam associated with the second side of the feature; and
    determining an asymmetry of the feature using the detected first reflected beam and the detected second reflected beam.

2. The method of claim 1, wherein detecting the first reflected beam or the second reflected beam comprises detecting a reflected beam intensity as a function of wavelength.

3. The method of claim 2, wherein detecting the first reflected beam or the second reflected beam further comprises detecting a reflected beam phase as a function of wavelength.

4. The method of claim 2, wherein determining a asymmetry of the feature comprises:
    comparing the reflected beam intensity of the first side and the second side to a database containing a plurality of intensity profiles associated with known feature characteristics; and
    determining a side profile associated with the first side and the second side of the feature, respectively, based on the comparison.

5. The method of claim 4, wherein determining a side profile associated with the first and second sides of the feature comprises correlating data associated with the first side and the second side of the feature to the plurality of profiles associated with known feature profiles, respectively, using a predetermined correlation threshold.

6. The method of claim 2, wherein the multiple wavelength components are within a range of wavelengths of about 100 nm to about 1000 nm.

7. The method of claim 1, wherein directing the second incident beam of radiation at a second side of a feature comprises positioning a wafer on a stage, wherein the stage rotates about 180 degrees from an original position to direct the second incident beam at the second side of the feature.

8. The method of claim 1, wherein directing the second incident beam of radiation at a second side of a feature comprises positioning a wafer on a stage wherein the second incident beam is rotated about the stage about 180 degrees from an original position of the first incident beam.

9. The method of claim 1, wherein detecting the first reflected beam or the second reflected beam comprises detecting a power spectral density as a function of spatial frequency intensity, wherein the power spectral density is proportional to a scattered intensity and is indicative of an amount of structure in some spatial frequency range.

10. The method of claim 1, wherein determining an asymmetry comprises comparing side profiles associated with the first and second sides of the feature to one another.

11. A method of determining asymmetry associated with a feature and generating process control data associated therewith, comprising the steps of:
    directing radiation at the feature;
    detecting reflected radiation from the feature;
    ascertaining an asymmetry of the feature using the detected reflected radiation; and
    generating process control data based on the asymmetry of the feature, wherein directing radiation comprises directing linearly polarized light at a non-perpendicular angle to a substrate having the feature thereon, wherein the linearly polarized light has a range of wavelengths of about 100 nm to about 1000 nm.

12. The method of claim 11, wherein detecting reflected radiation comprises:
    detecting a reflected radiation intensity distribution over the range of wavelengths; and
    detecting a reflected radiation phase distribution over the range of wavelengths.

13. The method of claim 12, wherein ascertaining the asymmetry of the feature comprises:
    correlating the detected reflected radiation intensity distribution and the detected reflected radiation phase distribution to a database containing a plurality of intensity distributions and phase distributions associated with known feature profile characteristics; and
    identifying a known feature profile characteristic which most has an intensity distribution and a phase distribution which most closely correlates to the detected reflected radiation intensity distribution and the detected reflected phase distribution of the feature.

14. The method of claim 11, wherein ascertaining the asymmetry of the feature comprises:
    determining an edge profile characteristic of a first side of the feature using at least a portion of the detected reflected radiation from the feature;
    determining an edge profile characteristic of a second, opposing side of the feature using at least a portion of the detected reflected radiation from the feature; and
    determining the asymmetry by analyzing the side profile characteristics associated with the first and second sides of the feature.

15. The method of claim 11, wherein the process control data comprises feedback process control data used to alter a semiconductor process step to reduce feature asymmetry in subsequent fabrication of like features.

16. The method of claim 11, wherein the process control data comprises feedforward process control data to alter a subsequent processing step related to the feature to thereby reduce an effect of the feature asymmetry.

17. The method of claim 11, wherein directing radiation at the feature comprises directing radiation at a substrate on which the feature resides at an angle which is approximately perpendicular thereto.

18. The method of claim 17, wherein detecting reflected radiation comprises detecting a reflected intensity distribution as a function of wavelength.

19. The method of claim 18, wherein ascertaining the asymmetry of the feature comprises:
   correlating the reflected intensity to a database containing a plurality of reflected intensity data sets having known feature profile characteristics;
   determining a feature profile by selecting a reflected intensity data set which most closely correlates to the detected reflected intensity; and
   determining the asymmetry from the known feature profile characteristics of the selected reflected intensity data set.

20. A method of maintaining a relatively spatially uniform dopant concentration is source/drain regions independent of an asymmetry gate electrode profile, comprising the steps of:
   directing radiation at a first side of a patterned gate electrode;
   detecting reflected radiation from the first side of the patterned gate electrode;
   directing radiation at a second, opposing side of the patterned gate electrode;
   detecting reflected radiation from the first side of the patterned gate electrode;
   determining a profile characteristic associated with the first and second sides of the patterned gate electrode using the detected reflected radiation associated with the first and second sides, respectively;
   determining an asymmetry of the patterned gate electrode using the determined profile characteristics of the first and second sides thereof; and
   generating ion implantation process control data associated with the asymmetry of the patterned gate electrode.

21. The method of claim 20, further comprising altering a tilt angle associated with an implantation of a source/drain region based on the ion implantation process control data, wherein the source/drain region is self-aligned with respect to the patterned gate electrode.

22. The method of claim 21, wherein the tilt angle is a function of the process control data based on an amount of asymmetry of the patterned gate electrode.

23. The method of claim 21, wherein altering the tilt angle comprises increasing the tilt angle directed at the side of the patterned gate electrode which has a sloped profile characteristic which is greater than a sloped profile characteristic of the opposing side of the patterned gate electrode.

24. A method of determining a feature profile using a database comprising:
   directing an incident beam of polarized light at a first side of a feature, wherein the polarized light comprises a range of wavelengths;
   detecting a phase of a first reflected beam, wherein the phase is a function of the range of wavelengths;
   detecting an intensity of a first reflected beam, wherein the intensity is a function of the range of wavelengths;
   directing an incident beam of polarized light at a second side of the feature, wherein the polarized light comprises a range of wavelengths;
   detecting a phase of a second reflected beam, wherein the phase is a function of the range of wavelengths;
   detecting an intensity of a second reflected beam, wherein the intensity is a function of the range of wavelengths; and
   correlating a first set of phase and intensity and a second set of phase and intensity as a function of the range of wavelengths with a database containing a plurality of intensity and phase data of known feature profiles to determine a profile of the feature.

25. The method of claim 24, wherein directing an incident beam of polarized light at a second side of the feature comprises rotating a stage about 180 degrees from an original position such that the incident beam is directed at the second side of the feature.

26. The method of claim 24, wherein directing an incident beam of polarized light at a second side of the feature comprises rotating the incident beam about the feature about 180 degrees from an original position.

27. The method of claim 24, further comprising the step of storing a first set and a second set of data associated with the phase and intensity as a function of wavelength for the first side and the second side, respectively, in a processor system comprising a memory, a database and a processor associated therewith such that the database communicates with the processor.

28. The method of claim 24, wherein the step of correlating comprises comparing a first set of phase and intensity and a second set of phase and intensity as a function of wavelength with the database and determining a profile based on a closest match.

29. A method of in-situ detection and control of asymmetry of a feature profile comprising:
   directing an incident beam of radiation at a first side of a feature;
   detecting a first reflected beam associated with the first side of the feature;
   directing an incident beam of radiation at a second side of the feature;
   detecting the second reflected beam associated with the second side of the feature;
   determining a pattern profile using the collected data from the first side and the second side of the feature; and
   changing one or more process parameters based on the determined pattern profile to reduce asymmetry as between the first side and the second side of the feature.

30. The method of claim 29, wherein directing an incident beam of radiation is performed using an ellipsometer.

31. The method of claim 30, wherein data collected from the first and second reflected beams is a reflected beam intensity as a function of wavelength.

32. The method of claim 30, wherein data collected from the first and second reflected beams is a reflected beam phase as a function of wavelength.

33. The method of claim 30, wherein determining a pattern profile using the collected data comprises correlating the data of a first side and a second side of the feature using a predetermined correlation threshold.

34. The method of claim 30, wherein determining a patten profile using the collected data comprises comparing the collected data from the first and the second sides of the feature with a database, wherein the database comprises sets of intensity and phase data corresponding to known feature profiles.

35. The method of claim 30, wherein an incident beam of radiation is an incident beam of polarized light having a predetermined range of wavelengths of about 100 nm to about 1000 nm.

36. The method of claim 29, wherein directing an incident beam of radiation at a second side of the feature comprises rotating a stage from an original position such that the incident beam is directed at a second side of the feature.

37. The method of claim 36, wherein the stage rotates about 180 degrees such that the incident beam is directed at a side opposite the first side.

38. The method of claim 29, wherein directing an incident beam of radiation at a second side of the feature comprises rotating the incident beam about the feature from an original position such that it is directed toward a second side of the feature.

39. The method of claim 38, wherein directing an incident beam of radiation at a second side of the feature comprises rotating the incident beam about the feature about 180 degrees from an original position such that it is directed toward a side opposite the first side.

40. The method of claim 29, wherein directing an incident beam of radiation is performed using a scatterometer.

41. The method of claim 40, wherein data detected by the detector is a power spectral density as a function of spatial frequency intensity, wherein the power spectral density is proportional to a scattered intensity and is indicative of an amount of structure in some spatial frequency range.

42. The method of claim 41, wherein determining a patten profile using the detected data comprises comparing the collected data from the first and the second sides of the feature with a database, wherein the database comprises sets of intensity and phase data corresponding to known feature profiles.

43. The method of claim 29, further comprising the step of storing a first set and a second set of data associated with the phase and intensity as a function of wavelength for the first side and the second side, respectively, in a processor system comprising a memory and a processor associated therewith.

44. The method of claim 29, wherein the processor system further comprises a database.

45. The method of claim 29, wherein the processor system further comprises a trained neural network.

46. The method of claim 29, wherein changing the process parameters comprises altering an etching process.

47. The method of claim 46, wherein altering the etching process further comprises altering a plasma chemistry in a plasma etching process to increase or decrease a slope of a sidewall of the feature, thereby improving a symmetry of subsequent features.

48. The method of claim 29, wherein changing the process parameters comprises altering one or more factors associated with chemical mechanical polishing pads to increase or decrease an amount of polishing on either the first or second sides or both sides of the feature.

49. The method of claim 29, wherein changing the process parameters comprises altering an alignment of the wafer to compensate for a coma effect of a stepper lens during an etching process.

* * * * *